US00PP09116P

United States Patent [19]

Kordes

[11] Patent Number: Plant 9,116

[45] Date of Patent: Apr. 25, 1995

[54] HYBRID TEA ROSE PLANT NAMED KORDABA

[75] Inventor: Wilhelm Kordes, Sparrieshoop, Germany

[73] Assignee: Bear Creek Gardens, Inc., Medford, Oreg.

[21] Appl. No.: 241,502

[22] Filed: May 12, 1994

[51] Int. Cl.[6] ..... A01H 5/00

[52] U.S. Cl. ..... Plt./16

[58] Field of Search ..... Plt. 11, 16, 17

*Primary Examiner*—Howard J. Locker

*Attorney, Agent, or Firm*—Klarquist Sparkman Campbell Leigh & Whinston

[57] ABSTRACT

A hybrid tea rose plant having a distinctive and novel flower color; excellent production; long vase life; thick, leathery petals, attractive, high-centered flower form, and few thorns.

1 Drawing Sheet

The present invention relates to a new and distinct variety of rose plant of the hybrid tea class which was originated by me by crossing the variety Korflapei, U.S. Plant Pat. No. 6,695, with an unnamed seedling (unpatented).

The primary objective of this breeding was to produce a new rose variety having the high cut-flower production, excellent vase life and lack of thorns of the female parent combined with the larger flower size and good flower form of the male parent. The objective was substantially achieved, along with other desirable improvements, as evidenced by the following unique combination of characteristics that are outstanding in the new variety and that distinguish it from its parents, as well as from all other varieties of which I am aware:

1. Thick, leathery petals;
2. Long vase life;
3. Novel petal coloring;
4. Excellent cut-flower production;
5. Few thorns; and
6. Attractive, high-centered flower form.

Asexual reproduction of this new variety by budding, as performed at Wasco, Calif., and Sparrieshoop, Germany, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Korflapei (U.S. Plant Pat. No. 6,695).

*Pollen parent.*—An unnamed seedling (unpatented).

Classification:

*Botanical.* 13 Rosa hybrida.

*Commercial.*—Hybrid tea.

FLOWER

Observations made from specimens grown in a greenhouse environment at Sparrieshoop, Germany, and Somis, Calif., from October, 1993, through March, 1994.

Blooming habit: Continuous.

Bud:

*Size.*—$1\frac{1}{2}$ inches long when the petals start to unfurl.

*Form.*—The bud form is long, pointed ovoid.

*Color.*—When sepals first divide, bud color is Orange Group 31A with a small area of Yellow Group 8D at the base of the petal. When half blown, the upper sides of the petals are Orange Group 30C except on the outer petal margins, where they are Greyed Red Group 180D; and the lower sides of the petals are Orange Group 30C.

*Sepals.*—Color: Green Group 137D. Surface texture: Covered in fine hairs. There are three normally to heavily appendaged sepals. There are two unappendaged sepals with hairy edges.

*Receptacle.*—Color: Green Group 137D. Shape: Funnel. Size: Broad ($\frac{3}{8}$ inch$\times\frac{3}{8}$ inch). Surface: Smooth, with occasional very fine hairs.

*Peduncle.*—Length: Medium (2–$2\frac{3}{4}$ inches). Surface: Smooth, with occasional very fine hairs, an occasional gland and a few very small prickles. Color: Medium green. Strength: Stiff, erect, heavy.

Bloom:

*Size.*—Medium. Average open size is $3\frac{3}{4}$–4 inches.

*Borne.*—Singly.

*Stems.*—Medium, strong. Average length is about 20–24 inches, with average 170 to 180 stems per square meter.

*Form.*—When first open: High centered. Permanence: Retains it form to the end, outer petals curl back, quill fashion.

*Petalage.*—Number of petals under normal conditions: 30–35.

*Color.*—The upper sides of the petals are Orange Group 30C changing on outer petal edges to Greyed Red Group 180D. The reverse sides of the petals are Orange Group 30C. The base of petals is Yellow Group 8D. The major color on the upper side is Orange Group 30C.

*Variegations.*—None.

*Discoloration.*—The general tonality at the end of the first day: No change. At the end of the third day: Outer petal margins change to Greyed Red Group 180D.

*Fragrance.*—Slight.

Petals:

*Texture.*—Thick, leathery.

*Shape.*—Round.

*Form.*—Edges moderately quilled.

*Arrangement.*—Imbricated, with a few small petaloids in the center.

*Persistence.*—Drop off cleanly.

*Lastingness.*—On the plant: Long (7–8 days). As a cut flower: Long (9–10 days).

Reproductive parts:

*Anthers.*—Size: Medium. Quantity: Many. Color: Yellow. Arrangement: Regular around styles.

*Filaments.*—Color: Reddish.

*Pollen.*—Color: Lemon yellow.

*Styles.*—Color: Greenish white with slight pink tint on the upper third of the style.

*Stigmas.*—Color: Greenish white.

Form: Bush.

Growth: Vigorous, upright, branching. Height in the greenhouse at one year (maturity) is 5–5½ feet. Width is 3–3½ feet.

Foliage: Number of leaflets on normal mid-stem leaves:

*Size.*—Large (6 inches long×4 inches wide).

*Quantity.*—Abundant.

*Color.*—New foliage: Underside: Greyed Orange 176C. Upper Surface: Greyed Orange 176C. Old foliage: Underside: Green Group 138A. Upper Surface: Green Group 139A.

Leaflets:

*Shape.*—Pointed oval.

*Texture.*—Upper side: Leathery.

*Edge.*—Serrated.

*Serration.*—Single, small.

*Petiole rachis.*—Color: Green.

*Petiole underside.*—Smooth.

*Stipules.*—Medium (½ inch long), serrated, bearded, glandular.

*Disease resistance.*—Resistant to mildew under normal growing conditions at Somis, Calif. Not tested for other diseases.

Wood:

*New wood.*—Color: Light green. Bark: smooth.

*Old wood.*—Color: Green. Bark: Smooth.

Prickles:

*Quantity.*—On main canes from base: few. On laterals from main canes: few.

*Form.*—Short, hooked downward.

*Color when young.*—Red.

Small prickles:

*Quantity.*—On main stalks: Few. On laterals: None.

*Color.*—Red.

I claim:

1. A new and distinct variety of rose plant of the hybrid tea class, substantially as herein shown and described, characterized particularly as to novelty by the unique combination of its distinctive and novel flower color; its excellent production; its long vase life; its thick, leathery petals; its attractive, high-centered flower form, and its few thorns.

* * * * *

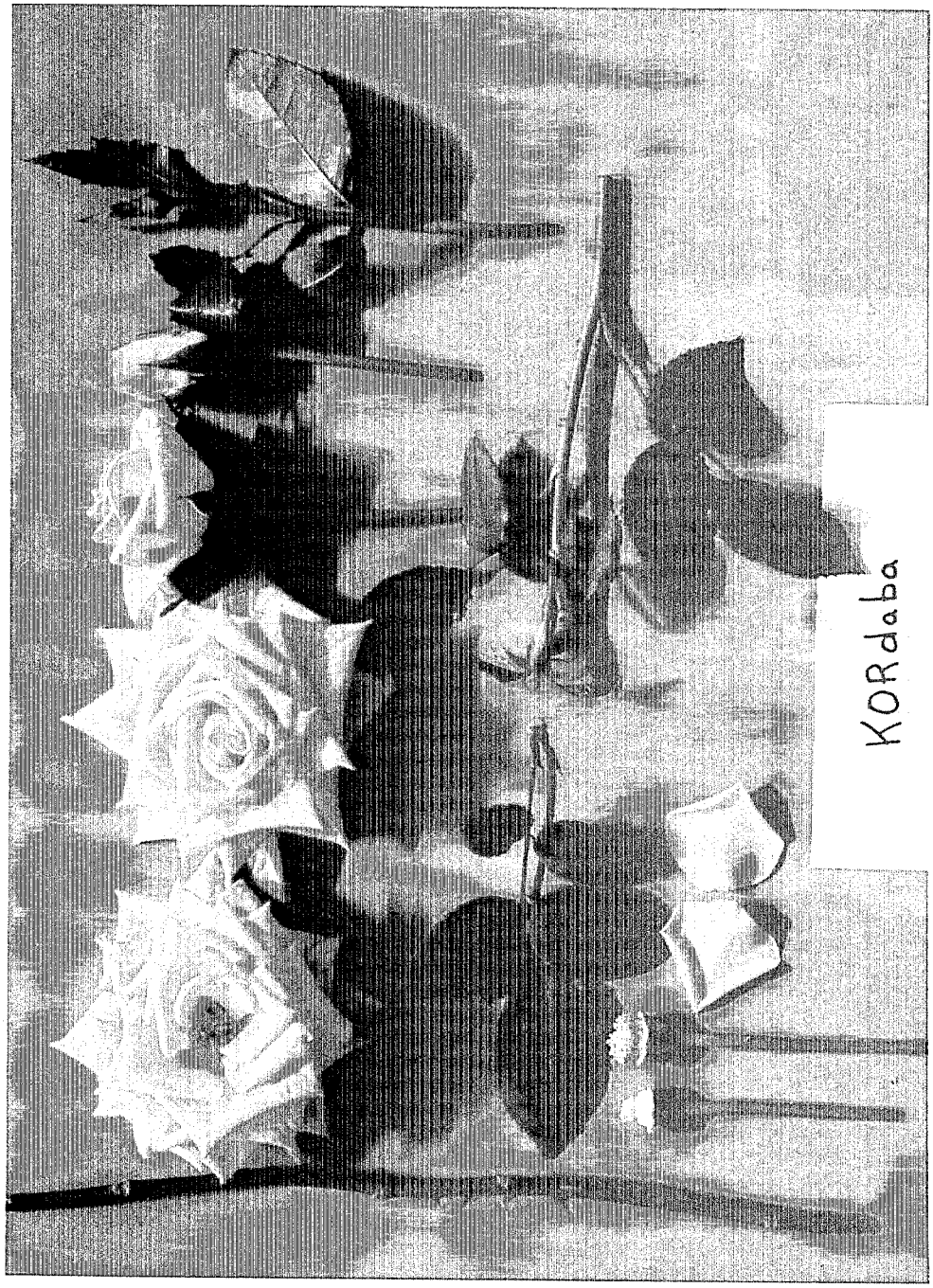
KORdaba

UNITED STATES PATENT AND TRADEMARK OFFICE

CERTIFICATE OF CORRECTION

PATENT NO. : PP 9,116

DATED : April 25, 1995

INVENTOR(S) : Wilhelm Kordes

It is certified that error appears in the above-identified patent and that said Letters Patent is hereby corrected as shown below:

Column 1, line 3, "Korflapei" should be --KORflapei--.

Column 1, line 39, "Korflapei" should be --KORflapei--.

Column 1, line 44, "Botanical. 13 Rosa hybrida" should be --Botanical. Rosa hybrida--.

Column 3, line 25, "leaves: " should be --leaves: 5.—.

Signed and Sealed this

Eighth Day of August, 1995

Attest:

Bruce Lehman

BRUCE LEHMAN

Attesting Officer

Commissioner of Patents and Trademarks